United States Patent [19]

Galons et al.

[11] Patent Number: 5,631,244

[45] Date of Patent: May 20, 1997

[54] MONO(6-AMINO-6-DEOXY)CYCLODEXTRIN DERIVATIVES SUBSTITUTED IN THE 6-POSITION BY AN α-AMINO ACID RESIDUE, PROCESS FOR THEIR PREPARATION AND THEIR USES

[75] Inventors: Hervé Galons, Paris; Jean Maignan, Tremblay les Gonesse, both of France; Jallal Gnaim, Garbiah, Israel

[73] Assignee: L'Oreal, Paris, France

[21] Appl. No.: 242,095

[22] Filed: May 13, 1994

[30] Foreign Application Priority Data

May 13, 1993 [FR] France ................. 93 05782

[51] Int. Cl.$^6$ ............... A61K 31/715; C08B 37/16
[52] U.S. Cl. ................ 514/58; 536/46; 536/103
[58] Field of Search ................ 514/58; 536/46, 536/103

[56] References Cited

FOREIGN PATENT DOCUMENTS

| 144170 | 6/1985 | European Pat. Off. . |
| 330241 | 8/1989 | European Pat. Off. . |
| 397985 | 11/1990 | European Pat. Off. . |
| 90/13100 | 9/1991 | WIPO . |

OTHER PUBLICATIONS

Hélène Parrot–Lopez et al., "Vectorised Transport of Drugs: Synthesis of new Glycosyl Derivative of Beta–cyclodextrin", Tetrahedron Letters, vol. 33, No. 2, Jan. 7, 1992, pp. 209–202.
Patent Abstracts Of Japan, vol. 13, No. 241, (C–604), Jun. 6, 1989, & JP–A–01 051 402 (Tosoh Corp), Feb. 27, 1989.
Ian J. G. Climie et al., "Labelling of Amino–acid Side–chains with 13C–labelled Electrophiles; Potential Application to the Probing of Active Sites of Enzymes", J. Chem. Soc., Chemical Communications 1975, pp. 160–161.
Ian J. G. Climie et al., "C–Nuclear Magnetic Resonance Spectroscopy as a probe of Enzyme Environment", Tetrahedron Letters, vol. 38, No. 5, 1982, pp. 697–711.
Masami Makita et al., "Gas–liquid chromatography of the N–isobutyloxycarbonyl methyl esters of non–protein amino acids", Journal of Chromatography, vol. 124, 1976, pp. 92–96, Amsterdam.

Primary Examiner—John Kight
Assistant Examiner—Everett White
Attorney, Agent, or Firm—Oliff & Berridge

[57] ABSTRACT

Mono (6-amino-6-deoxy)cyclodextrin derivatives substituted in the 6-position by an α-amino acid residue. These derivatives correspond to the following general formula:

$$CD-NH-CO-CH_2-(Z)_n-\underset{\underset{COOH}{|}}{CH}-NH_2 \qquad (I)$$

in which:

CD represents α-, β- or γ-cyclodextrin, n is 0 or 1, and

Z represents a divalent radical chosen from:
  (i) $-CH_2$
  (ii) $-O-CH_2-$
  (iii) $-S-CH_2-$, $$(iv) -O-\underset{\underset{CH_3}{|}}{CH}-,$$

and (v) $-O-C_6H_4-CH_2-$.

These derivatives find an application in the formation of inclusion complexes of active substances and can be used in various fields, in particular in cosmetics, in dermatology and in pharmacology.

8 Claims, No Drawings

MONO(6-AMINO-6-DEOXY)CYCLODEXTRIN DERIVATIVES SUBSTITUTED IN THE 6-POSITION BY AN α-AMINO ACID RESIDUE, PROCESS FOR THEIR PREPARATION AND THEIR USES

The subject of the present invention is new mono(6-amino-6-deoxy) cyclodextrin derivatives substituted in the 6-position by an α-amino acid residue, their process of preparation and their uses in various fields of industry, in particular in cosmetics, pharmacology and dermatology, these new derivatives being capable of forming inclusion complexes, These new cyclodextrin derivatives can also find applications in other fields, especially in analytical chemistry, in the farm produce industry and also as a sequestering agent for certain transition metals.

Use of carrier molecules capable of increasing the solubility in aqueous medium of lipophilic substances or of stabilizing substances which are supposed to be unstable in aqueous medium or alternatively of obtaining a targeted release, as a function of time or of the surrounding environment, of an active principle is very particularly sought after in the cosmetics, pharmaceutical and dermatological fields.

It has thus been proposed, in Patent Application PCT WO 91/13100, to use cyclodextrins substituted by various groups, especially by carboxylic acid functional groups.

This patent application describes in particular the preparation and use of cyclodextrin derivatives resulting from the reaction of mono(6-amino-6-deoxy)-β-cyclodextrin with a dicarboxylic anhydride such as succinic anhydride or glutaric anhydride.

The derivatives obtained, which carry a free carboxylic acid functional group, have a better solubility but the latter nevertheless remains unsatisfactory for certain applications and moreover require an at least partial prior neutralization of the carboxylic acid functional groups.

After various research studies carried out on cyclodextrins, it was entirely unexpectedly and surprisingly observed that a new class of cyclodextrin derivatives made it possible to overcome the disadvantages encountered until now, especially those of the cyclodextrin derivatives of Application PCT WO 91/13100.

The new cyclodextrin derivatives according to the invention not only present the advantage of having a markedly greater solubility than the previously known and used derivatives but also of being able to be employed directly, that is to say without prior neutralization, while being inoffensive and well tolerated by the mucous-membranes and the skin.

These main advantages are due essentially to the presence on the cyclodextrin molecule of an α-amino acid residue so that, in aqueous medium, the cyclodextrin derivatives according to the invention exist in the bipolar or zwitterionic form.

The subject of the present invention is therefore, as new industrial products, mono(6-amino-6-deoxy)cyclodextrin derivatives substituted in the 6-position by an α-amino acid residue, these derivatives corresponding to the following general formula:

$$CD-NH-CO-CH_2-(Z)_n-\underset{\underset{COOH}{|}}{CH}-NH_2 \qquad (I)$$

in which:

CD represents α-, β- or γ-cyclodextrin, n is 0 or 1, and

Z represents a divalent radical chosen from:
(i) —$CH_2$—
(ii) —O—$CH_2$—
(iii) —S—$CH_2$—

(iv) —O—$\underset{\underset{CH_3}{|}}{CH}$—, and (v) —O—$C_6H_4$—$CH_2$—.

According to a preferred embodiment of the invention, the CD radical is β-cyclodextrin.

Mention may especially be made, among the cyclodextrin derivatives of general formula (I), of:

mono[N-(4-amino-4-carboxy butyryl)amino]-6-deoxy β-cyclodextrin, mono[N-(3-amino-3-carboxy propionyl)amino]-6-deoxy β-cyclodextrin, mono[N-4-(2'-amino 2'-carboxy ethyl) 1-(phenyloxymethylcarbonyl) amino]-6-deoxy β-cyclodextrin.

Another subject of the present invention is the process for the preparation of the cyclodextrin derivatives of general formula (I), it being possible for this process to be represented by the following reaction diagram:

Diagram I $$CDNH_2 + HOOC-CH_2-(Z)_n-\underset{\underset{COOR_2}{|}}{CH}-NH-COOR_1$$
(1)                       (2)

$$\downarrow$$

$$CD-NH-CO-CH_2-(Z)_n-\underset{\underset{COOR_2}{|}}{CH}-NH-COOR_1$$

$$\downarrow (3)$$

$$CD-NH-CO-CH_2-(Z)_n-\underset{\underset{COOH}{|}}{CH}-NH_2$$
(I)

CD, Z and n have the same meanings as those given for the formula (I), $R_1$ represents the tert-butyl radical or the benzyl radical, and $R_2$ represents the methyl radical or the benzyl radical.

This process consists in reacting an α-aminodicarboxylic acid (2) in the L,D or racemic forms (the α-amino acid functional group of which has been protected) with a (6-amino-6-deoxy) cyclodextrin (1) in solution in an organic solvent such as dimethylformamide in the presence of an excess of 1-hydroxybenzotriazole not exceeding 20 mol % with respect to the protected α-aminodicarboxylic acid (2) and of an excess of dicyclohexylcarbodiimide not exceeding 30 mol % with respect to the protected α-aminodicarboxylic acid (2). The reaction is generally carried out with stirring until the starting materials have completely disappeared and the mixture is then filtered with a view to removing the dicyclohexylurea formed. After concentrating under vacuum, the amide obtained (3) is recrystallized, preferably from water.

According to a preferred embodiment, the molar ratio between the compounds (1) and (2) is generally between 1 and 1.5.

The protected functional groups of the compound (3) are then deprotected under operating conditions which depend on the nature of the protecting groups used.

Thus, the benzyloxycarbonyl and benzyl groups are displaced by hydrogenation in the presence of Pd/C (5 to 10%) and the tert-butyloxycarbonyl groups are cleaved in the presence of trifluoroacetic acid, the methyl ester functional groups being removed by saponification in the presence of 1N sodium hydroxide solution.

(6-Amino-6-deoxy)-β-cyclodextrin (1) is a known product, prepared according to known methods, for example that described in U.S. Pat. No. 5,068,227. Some of the compounds of formula (2) are also commercially available from the Company Bachem, in particular benzyl N-(benzyloxycarbonyl)aspartate (n=0 and $R_1$ and $R_2$=—$CH_2C_6H_5$) and benzyl N-(benzyloxycarbonyl)glutamate (Z=—$CH_2$— and $R_1$ and $R_2$=—$CH_2C_6H_5$).

The other compounds of formula (2) and their precursors in which Z is other than —$CH_2$— are novel and can be represented by the following general formula:

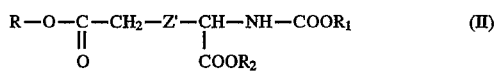

in which:

R represents a hydrogen atom or the benzyl radical, $R_1$ represents the tert-butyl radical or the benzyl radical, $R_2$ represents the methyl radical or the benzyl radical, and Z' represents a divalent radical chosen from:

(i) —O—$CH_2$—

(ii) —S—$CH_2$—

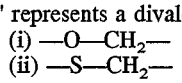

and (iv) —O—$C_6H_4$—$CH_2$—.

The intermediate compounds of formula (II) are obtained according to the following reaction diagram:

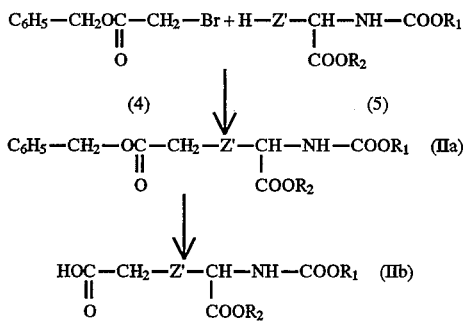

The H—Z'— group represents the

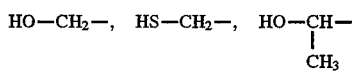

or p-HO—$C_6H_4$—$CH_2$— radical, and $R_1$ and $R_2$ have the same meanings as those given above for the formula (II).

The synthesis of these compounds consists in reacting benzyl bromoacetate (4) with a protected ω-hydroxy- or ω-mercapto-α-amino acid of formula (5) in organic solvent medium, preferably in dimethylformamide, in the presence of lithium hydride, which makes it possible to obtain the O- or S-alkylation derivative of formula (IIa) with a good yield.

The corresponding acid (IIb) is obtained by hydrogenation in methanol/methylene chloride solution in the presence of 5% Pd/C.

The protected ω-hydroxy-α-amino acids of formula (5) are in some cases known, in particular methyl N-(tert-butyloxycarbonyl)tyrosinate (H—Z'=p-HO—$C_6H_4$—$CH_2$—, $R_1$=C($CH_3$)$_3$ and $R_2$=—$CH_3$), which is marketed by the Company Bachem.

The other compounds of formula (5) can easily be obtained from α-amino acids such as serine, threonine and cysteine according to conventional methods for the protection of α-amino acid functional groups.

Mention may especially be made, among the novel intermediate compounds of formula (II), of methyl N-(tert-butyloxycarbonyl)-O-(benzyloxycarbonylmethyl)tyrosinate and methyl N-(tert-butyloxycarbonyl)-O-(carboxymethyl) tyrosinate.

The cyclodextrin derivatives according to the invention find an application in various industrial fields.

These cyclodextrin derivatives can especially be used as such, that is to say without inclusion of active ingredient, especially in cosmetic or dermatological compositions in the treatment of the skin or hair, the cyclodextrin derivatives being capable of having a plasticizing effect.

According to this embodiment, the cyclodextrin derivatives according to the invention are generally present at a concentration of between 0.1 and 10% by weight with respect to the total weight of the composition.

However, the use of cyclodextrin derivatives according to the invention is more particularly directed towards the formation of inclusion complexes of various active substances. The latter are preferably substances of lipophile type or else alternatively products which are insoluble or unstable in aqueous medium and are more particularly chosen from the active principles used in the cosmetic, dermatological and pharmaceutical fields.

As mentioned above, the property of the cyclodextrin derivatives according to the invention of being able to exist in the zwitterionic form makes it possible to increase the solubility of these active principles which, until now, could not be satisfactorily obtained.

Mention may especially be made, among active substances which can form inclusion complexes or which can be stabilized, of:

anti-oxidizing agents and compounds which act against free radicals such as butylhydroxytoluene (B.H.T.), butylhydroxyanisole (B.H.A.), vitamin E or derivatives of para-(tert-butyl)benzylidenecamphor, such as those described in French Patent No. 2,624,508 and in particular 3-(3',5'-di(tert-butyl)-4'-hydroxy) benzylidenecamphor, anti-acne, anti-aging or anti-photoaging agents such as retinoic acid and its isomers as well as certain derivatives of the latter such as those described in Application EP 465,343, in Applications WO 91/00793, in French Application No. 91 05394 or alternatively in Application EP 514,264, or such as retinol and its esters, especially the acetate or the palmitate, agents for controlling psoriasis such as anthralin, psoralens or aromatic retinoids such as tigason and its derivatives or such as 6-[3-(1-adamant-yl)-4-methoxyphenyl]-2-naphthoic acid, preserving and bactericidal agents, such as substituted isothiazolones, agents promoting hair regrowth or preventing its loss such as minoxidil and its derivatives or the products described in French Patent Applications 2,606,635, 2,607,505, 2,618,068, 2,654,101 or 2,663,327 and Applications EP 304,649, EP 304,665, EP 353,323, EP 303,871, EP 356,271, EP 464,034, EP 177,581, EP 420,507, EP 408,442 and EP 459,890, sunscreening agents, agents for hydrating and/or plasticizing the stratum corneum such as α-hydroxyacids, thiamorpholinone derivatives such as those described in French Patents No. 2,525,106 and 2,525,220, pyrrolidonecarboxylic acid and the serines, or salicylated derivatives such as those described in Application EP 378,936 and especially 5-(n-octanoyl)salicylic acid, agents for reconstituting the lipid barrier such as ceramides and their derivatives, in particular those described in French Patent No. 2,588,256 and in Applications EP 420,722 and EP 500,437, hair dyes which are difficult to dissolve in aqueous media such as anthraquinone dyes, azo dyes and nitro derivatives of the benzene series, or alternatively dyes which can be stabilized, such as substituted indolines and indoles, depigmenting agents such as hydroquinone, kojic acid or arbutin and its derivatives, anti-inflammatory agents such as inhibitors of lipoxygenase and/or of cyclooxygenase, steroids such as hydrocortisone and 17-hydroxycorticosterone, anti-viral and anti-cancer agents such as 5-fluorouracil.

The cosmetic, pharmaceutical or dermatological compositions containing such inclusion complexes can be provided in various forms, especially in the form of aqueous or aqueous/alcoholic lotions, of gels or of dispersions and are present in a proportion of between 0.1 and 30% with respect to the total weight of the compositions.

The cyclodextrin derivatives according to the invention are also capable of forming inclusion complexes with certain metal salts, especially the metal salts which take part in the oxidation-reduction process during hair dyeing or bleaching or during dyeing or controlling aging of the skin.

The cyclodextrin derivatives according to the invention additionally find certain applications in the formation of complexes with amino acid molecules via a transition metal which makes it possible thus to sequester these metals, the cyclodextrin derivatives according to the invention then being capable of acting as protective or detoxifying agents of these metals, especially in cosmetic products.

A good many other uses can be envisaged for the cyclodextrin derivatives according to the invention, especially in capillary electrophoresis, as chromatographic chiral phase, or alternatively in the formation of complexes in the farm produce field.

A number of examples of the preparation of the cyclodextrin derivatives according to the invention, and of the use of these derivatives, will now be given by way of illustration.

PREPARATION EXAMPLES

Visualisation of the silica thin layer chromatography (TLC) plates was carried out by UV or after spraying with 10% $H_2SO_4$ and then heating or by ninhydrin in solution in ethanol and then heating. The NMR spectra were recorded on a Brucker 270 apparatus (Internal reference TMS).

EXAMPLE 1

Preparation of mono[N-(4-amino-4-carboxy butyryl)amino]-6-deoxy-β-cyclodextrin (a) Mono [N-(4-benzyloxycarbonylamino-4-benzyloxy carbonyl butyryl)amino]-6-deoxy-β-cyclodextrin 0.209 g of 1-hydroxybenzotriazole and 0.385 g $(1.855 \cdot 10^{-3}$ mol) of dicyclohexylcarbodiimide are added to a solution of 0.635 g $(1.6 \cdot 10^{-3}$ mol) of benzyl N-benzyloxycarbonylamino-α-glutamate in 20 ml of dimethylformamide (DMF). After stirring for 30 minutes at 20° C., 1.5 g $(1.325 \cdot 10^{-3}$ mol) of mono(6-amino-6-deoxy)-β-cyclodextrin are added and the mixture is stirred for 24 hours at room temperature. After filtering the dicyclohexylurea, the organic solution is concentrated under vacuum. The solid obtained is recrystallized from water and exists, after drying, in the form of a colourless solid having a melting point greater than 240° C. (Yd: 68–78%).

TLC: $R_f$=0.38 (eluent: ethyl acetate: 36%, isopropanol: 36%, concentrated aqueous ammonia: 21%, water: 7%).

NMR ($d_6$-DMSO): $CH_2CH_2CO$=1.83–1.93, $CH_2CH_2CO$=2.25, CH—$CH_2$=4.10, anomeric protons= 4.82, $CH_2C_6H_5$=5.01, $CH_2C_6H_5$=5.10, $C_6H_5$=7.31–7.34.

(b) Mono[N-(4-amino 4-carboxy butyryl)amino]-6-deoxy-β-cyclodextrin 200 mg of Pd/C (10%) are added to a solution of 1.5 g $(1 \cdot 10^{-3}$ mol) of the compound obtained in (a) above in a mixture of 20 ml of water and 50 ml of methanol and the mixture is then stirred vigorously at 20° C. under hydrogen for 6 hours. After removal of the hydrogen, the mixture is filtered, the catalyst is rinsed with 3 times 5 ml of water and the filtrate is concentrated under vacuum. A colourless solid is obtained having a melting point greater than 240° C. with a yield of 86%.

TLC: $R_f$=0.20 (eluent: identical to 1(a) above).

NMR ($d_6$-DMSO): $CH_2CH_2CO$=1.90, $CH_2CH_2CO$=2.29, anomeric protons=4.82–4.85, β-CD=3.29–3.35 and 3.56–3.65.

Solubility in water greater than 1000 g/l.

EXAMPLE 2

Preparation of mono[N-(3-amino 3-carboxy propionyl)amino]-6-deoxy-β-cyclodextrin (a) Mono [N-(3-benzyloxycarbonylamino 3-benzyloxycarbonyl propionyl)amino]-6-deoxy β-cyclodextrin 0.209 g of 1-hydroxybenzotriazole and 0.385 g $(1.855 \cdot 10^{-3}$ mol) of dicyclohexylcarbodiimide are added to a solution of 0.611 g $(1.6 \cdot 10^{-3}$ mol) of benzyl N-(benzyloxycarbonyl)aspartate in 20 ml of dimethylformamide. After stirring for 30 minutes at 20° C., 1.5 g $(1.325 \cdot 10^{-3}$ mol) of mono(6-amino-6-deoxy)-β-cyclodextrin are added and the mixture is then stirred for 24 hours at room temperature.

The dicyclohexylurea formed is filtered and the organic solution is then concentrated under vacuum. The solid obtained is recrystallized from water.

A colourless solid is obtained with a melting point greater than 240° C. and with a yield between 71 and 86%.

TLC: $R_f$=0.62 (eluent: ethyl acetate: 36%, isopropanol: 36%, concentrated aqueous ammonia: 21%, water: 7%).

NMR: ($d_6$-DMSO)=$CH_2CO$: 3.05 and 3.15, β-CD: 3.30 and 3.68, anomeric protons: 4.82, hydroxyl protons: 5.61–5.74, $C_6H_5$: 7.33–7.37.

(b) Mono [N-(3-amino 3-carboxy propionyl)amino]-6-deoxy β-cyclodextrin 200 mg of Pd/C (10%) are added to a solution of 1.48 g $(1 \cdot 10^{-3}$ mol) of the compound obtained in (a) above in a mixture of 20 ml of water and 50 ml of methanol and the mixture is then stirred vigorously at 20° C. under hydrogen for 6 hours.

After removal of the hydrogen, the mixture is filtered, the catalyst is rinsed 3 times with 5 ml of water and the filtrate is then concentrated under vacuum.

A colourless solid is obtained, with a melting point greater than 240° C. and with a yield of 91%.

Solubility in water greater than 1000 g/l.

TLC: $R_f=0.375$ (eluent identical to that used in 2(a) above).

NMR: ($d_6$-DMSO)=$CH_2CO$: 2.90, β-CD: 3.31 and 3.73, anomeric protons: 4.82, hydroxyl protons: 5.65–5.79.

EXAMPLE 3

Preparation of mono [N-4-(2'-amino 2'-carboxy ethyl) 1-(phenyloxymethylcarbonyl)amino]6-deoxy β-cyclodextrin A) Mono [N-4-(2'-tertiobutyloxycarbonylamino 2'-methoxy carbonyl ethyl) 1-(phenyloxymethylcarbonyl) amino]6-deoxy β-cyclodextrin (a) 0.165 g (20.5·$10^{-3}$ mol) of lithium hydride is added, at room temperature, to a solution of 5.5 g (18.7·$10^{-3}$ mol) of methyl N-(tert-butyloxycarbonyl)tyrosinate. After stirring for 15 minutes, 4.719 g (20.5·$10^3$ mol) of benzyl bromoacetate are added. The mixture is stirred for 5 hours at 40° C., then concentrated under vacuum and the O-alkylation product is separated by chromatography on silica by elution using a 50% ethyl acetate and 50% petroleum ether mixture. A colourless oil is obtained, with a yield of 82%.

TLC: $R_f=0.92$ (eluent: 100% ethyl acetate), $R_f=0.30$ (eluent: 50% ethyl acetate, 50% cyclohexane).

NMR ($CDCl_3$): $(CH_3)_3C$=1.42, $CH_2$—$C_6H_4$=3.05, $OCH_3$=3.7, $CHCH_2$=4.6, $OCH_2CO$=4.64, NH=4.95, $CH_2C_6H_5$=5.25, CH aro(aryloxy)=6.83 and 7.03, aro (benzyl)=7.27–7.37.

(b) The product obtained is taken up in 50 ml of a mixture of 50% methanol and 50% methylene chloride, 50 mg of Pd/C (5%) are then added to the solution and the mixture is stirred under a hydrogen atmosphere.

When hydrogen absorption has ceased (after approximately 50 min), the mixture is filtered, the catalyst is rinsed twice with 10 ml of methylene chloride and the solution is then evaporated.

A yellow oil is obtained with a yield of 96%.

TLC: $R_f=0.45$ (eluent: 100% ethyl acetate)

$R_f=0.15$ (eluent: 50% ethyl acetate/50% cyclohexane).

NMR ($CDCl_3$): $(CH_3)_3C$=1.45, $CH_2$—$C_6H_4$=3.01, $OCH_3$=3.72, $CHCH_2$=4.53, $OCH_2CO$=4.64, NH=4.95, CH aro(aryloxy)=6.81 and 7.02.

(c) The acid thus obtained is then reacted with (6-amino-6-deoxy)-β-cyclodextrin under the same conditions as those of Example 1(a).

The expected product is obtained in the form of a colourless solid with a yield of 78%.

TLC: $R_f=0.30$ (eluent: 36% ethyl acetate, 36% isopropanol, 21% concentrated aqueous ammonia, 7% water).

NMR (DMSO+$D_2O$): $C(CH_3)_3$=1.43, β-C+$OCH_3$=3.2–3.4 and 3.5–3.6, $CHCH_2$=4.50, $OCH_2CO$=4.6, CH aro (aryloxy)=6.83 and 7.08.

B) Mono [N-4-(2'-amino 2'-carboxy ethyl) 1-(phenyloxymethylcarbonyl)amino]6-deoxy β-cyclodextrin The compound obtained in (A)(c) above is dissolved in 10 ml of a 1:1 solution of trifluoroacetic acid in methylene chloride. After 2 hours at room temperature, the mixture is concentrated, is take up in 10 ml of water and then 30 ml of a 1N sodium hydroxide solution are added. After stirring for 3 hours at room temperature, the mixture is concentrated under vacuum and the solid taken up again with water. After purification on a Sephadex column, the product is lyophilized.

A colourless powder is obtained, with a melting point greater than 240° C. and with a yield of 76%.

NMR (DMSO): β-CD, 3.2–3.4 and 3.5–3.6, anomeric protons=4.85, aromatic protons=6.87 and 7.12.

TLC: $R_f=0.23$ (eluent : ethyl acetate: 36%, isopropanol: 36%, concentrated aqueous ammonia: 21%, water: 7%).

Solubility in water: 900 g/l.

EXAMPLES OF USE

EXAMPLE A

Inclusion complex of minoxidil in mono [N-(3-amino 3-carboxy propionyl)amino]-6-deoxy β-cyclodextrin 22 mg of minoxidil are added, at 70° C., to a solution of 114 mg of the compound prepared in Example 2(b) in 0.3 ml of water. After stirring for 15 minutes at 70° C., the mixture is cooled to room temperature and then filtered. The clear solution obtained is lyophilized.

According to quantitative determinations carried out by HPLC and by NMR, this complex contains 15.4% of minoxidil, which corresponds to a ratio of 1.1 molecule of minoxidil per 1 molecule of the compound of Example 2(b).

The inclusion of minoxidil in the cyclodextrin derivative according to Example 2(b) increases its solubility in water by a factor of the order of 40, the latter then being 110 g/l.

EXAMPLE B

Inclusion complex of minoxidil in mono [N-(4-amino 4-carboxy butyryl)amino]-6-deoxy β-cyclodextrin An inclusion complex of minoxidil in mono [N-(4-amino 4-carboxy butyryl)amino]-6-deoxy β-cyclodextrin is prepared from 128 mg of the compound prepared in Example 1(b) and from 21 mg of minoxidil according to the same procedure as described in Example A.

According to quantitative determination carried out by NMR, this complex contains 1 molecule of minoxidil per 1 molecule of the compound of Example 1(b).

The inclusion of minoxidil in the cyclodextrin derivative according to Example 1(b) increases its solubility in water by a factor of the order of 40, the latter then being 110 g/l.

EXAMPLE C

Inclusion complex of 5-fluorouracil in mono [N-(4-amino 4-carboxy butyryl)amino]-6-deoxy β-cyclodextrin An inclusion complex of 5-fluorouracil in mono [N-(4-amino 4-carboxy butyryl)amino]-6-deoxy β-cyclodextrin is prepared from 128 mg of the compound prepared in Example 1(b) and from 13 mg of 5-fluorouracil according to the same procedure as described in Example A.

According to quantitative determination carried out by NMR, this complex contains 1 molecule of 5-fluorouracil per 1 molecule of the compound of Example 1(b).

The inclusion of 5-fluorouracil in the cyclodextrin derivative according to Example 1(b) increases its solubility in water by a factor of the order of 100, the latter then being 80 g/l.

EXAMPLE D

Inclusion complex of 6-[3-(1-adamantyl)-4-methoxyphenyl]-2-naphthoic acid in mono [N-(4-amino 4-carboxy butyryl)amino]-6-deoxy β-cyclodextrin An inclusion complex of 6-[3-(1-adamantyl)-4-methoxyphenyl]-2-naphthoic acid in mono [N-(4-amino 4-carboxy butyryl)amino] -6-deoxy β-cyclodextrin is prepared from 128 mg of the compound prepared in Example 1(b) and from 10 mg of 6-[3-(1-adamantyl) -4-methoxyphenyl]-2-naphthoic acid according to the same procedure as described in Example A.

According to quantitative determination carried out by NMR, this complex contains 1 molecule of 6-[3-(1-adamantyl)-4-methoxyphenyl]-2-naphthoic acid per 8 molecules of the compound of Example 1(b).

The inclusion of 6- [3- (1-adamantyl) -4-methoxyphenyl] -2-naphthoic acid in the cyclodextrin derivative according to Example 1(b) increases its solubility in water by a factor of the order of 1,000, the latter then being 4 g/l.

EXAMPLE E

Inclusion complex of 17-hydroxycorticosterone in mono [N-(4-amino 4-carboxy butyryl)amino]-6-deoxy β-cyclodextrin An inclusion complex of 17-hydroxycorticosterone in mono [N-(4-amino 4-carboxy butyryl)amino]-6-deoxy β-cyclodextrin is prepared from 128 mg of the compound prepared in Example 1(b) and from 20 mg of 17-hydroxycorticosterone according to the same procedure as described in Example A.

According to quantitative determination carried out by NMR, this complex contains 1 molecule of 17-hydroxycorticosterone per 2 molecules of the compound of Example 1(b).

The inclusion of 17-hydroxycorticosterone in the cyclodextrin derivative according to Example 1(b) increases its solubility in water by a factor of the order of 200, the latter then being 11 g/l.

We claim:

1. A mono(6-amino-6-deoxy) cyclodextrin derivative substituted in the 6-position by an α-amino acid residue, corresponding to the following formula:

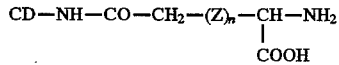  (I)

in which:

CD represents α-, β- or γ-cyclodextrin, n is 0 or 1, and

Z represents a divalent radical selected from the group consisting of:

(i) —O—CH$_2$—

(ii) —S—CH$_2$—

(iii) 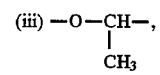

and (iv) —O—C$_6$H$_4$—CH$_2$—.

2. The cyclodextrin derivative according to claim 1, wherein the cyclodextrin is β-cyclodextrin.

3. The cyclodextrin derivative according to claim 1, wherein said cyclodextrin derivative is mono[N-4-(2'-amino 2'-carboxy ethyl) 1-(phenyloxymethylcarbonyl) amino]-6-deoxy β-cyclodextrin.

4. Cosmetic or dermatological composition, containing from 0.1 to 10% by weight of at least one cyclodextrin derivative according to claim 1.

5. A method of making inclusion complexes of the cyclodextrin derivatives according to claim 1 and active substances of a lipophile nature or which are insoluble or unstable in aqueous medium comprising reacting said cyclodextrin derivative with said active substance.

6. Method according to claim 5, wherein the active substances are selected from the group consisting of antioxidizing agents, compounds which are active against free radicals, anti-acne agents, anti-aging agents, anti-psoriatic agents, preserving agents, bactericidal agents, agents promoting hair regrowth, agents for hydrating and/or plasticizing the stratum corneum, sunscreening agents, agents for reconstituting the lipid barrier, hair dyes, depigmenting agents, anti-inflammatory agents, anti-viral agents, anti-cancer agents and steroids.

7. Cosmetic or dermatological composition, containing an inclusion complex formed by the method of claim 5.

8. Cosmetic or dermatological composition according to claim 7, which contains the inclusion complex in a proportion of between 0.1 and 30% with respect to the total weight of the composition.

* * * * *